(12) United States Patent
Hirao

(10) Patent No.: US 10,415,077 B2
(45) Date of Patent: Sep. 17, 2019

(54) METHOD OF REDUCING MEASUREMENT ERROR CAUSED BY CATALASE INHIBITION BY AZIDE

(75) Inventor: Yuhko Hirao, Gosen (JP)

(73) Assignee: DENKA SEIKEN CO., LTD., Tokyo (JP)

( * ) Notice: Subject to any disclaimer, the term of this patent is extended or adjusted under 35 U.S.C. 154(b) by 968 days.

(21) Appl. No.: 12/677,676

(22) PCT Filed: Sep. 11, 2008

(86) PCT No.: PCT/JP2008/066377
§ 371 (c)(1),
(2), (4) Date: Mar. 11, 2010

(87) PCT Pub. No.: WO2009/035015
PCT Pub. Date: Mar. 19, 2009

(65) Prior Publication Data
US 2011/0171672 A1 Jul. 14, 2011

(30) Foreign Application Priority Data
Sep. 12, 2007 (JP) .................... 2007-236242

(51) Int. Cl.
*C12Q 1/30* (2006.01)
(52) U.S. Cl.
CPC ..................................... *C12Q 1/30* (2013.01)
(58) Field of Classification Search
CPC ........................................................ C12Q 1/30
See application file for complete search history.

(56) References Cited

U.S. PATENT DOCUMENTS

| | | | | |
|---|---|---|---|---|
| 5,055,398 | A * | 10/1991 | Fujie ...................... | C12Q 1/26 435/10 |
| 5,998,216 | A * | 12/1999 | O'Donnell ............. | A61K 47/42 252/380 |
| 2003/0190368 | A1* | 10/2003 | Stoughton ............... | A61K 38/57 424/556 |
| 2006/0154374 | A1 | 7/2006 | Itoh et al. | |

FOREIGN PATENT DOCUMENTS

| | | |
|---|---|---|
| EP | 0 887 422 A1 | 12/1998 |
| JP | 2-76579 A | 3/1990 |
| JP | 4-20288 A | 1/1992 |
| JP | 10-14596 * | 1/1998 |
| JP | 11-46760 A | 2/1999 |
| JP | 2003-274996 A | 9/2003 |
| JP | 2004-049063 A | 2/2004 |

OTHER PUBLICATIONS

Kikuchi-Torii et al. (Properties of Aspergillus niger catalase, 1982, Journal of Biochemistry, vol. 92, pp. 1449-1456).*
Switala et al. (Diversity of properties among catalases, 2002, Archives of Biochemistry and Biophysics, vol. 401, pp. 145-154).*
Uppu et al. (Biphasic synthesis of high concentrations of peroxynitrite using water-insoluble alkyl nitrite and hydrogen peroxide, 1996, Methods in Enzymology, vol. 269, pp. 322-329).*
Shizuo et al. (English translation of JP10-14596, 1998, 10 pages).*
Lichstein, et al. J Bacteriol., 1944, 47(3):231-238.*
Gruft et al. Can. J. Biochem., 1978, 56:916-919.*
Whittenbury, J. gen. Microbiol., 1964, 35:13-26.*
Extended European Search Report dated Jun. 27, 2012, in European Patent Application No. 08830181.7.
Hirano et al., "A novel and simple method for quantification of small, dense LDL," J. Lipid Res. (2003), vol. 44, pp. 2193-2201.
Johnston et al., "Distribution and Characteristics of the Catalases of Lactobacillaceae," Journal of Bacteriology (Aug. 1965), vol. 90, No. 2, pp. 347-351.
Johnston et al., "Isolation and Characterization of the Cyanide-Resistant and Azide-Resistant Catalase of Lactobacillus plantarum," Journal of Bacteriology (Aug. 1965), vol. 90, No. 2, pp. 352-356.
Kikuchi-Torii et al., "Properties of Aspergillus niger Catalase," J. Biochem. (1982), vol. 92, No. 5, pp. 1449-1456.
Switala et al., "Diversity of properties among Catalases," Archives of Biochemistry and Biophysics (2002), vol. 401, pp. 145-154.

* cited by examiner

*Primary Examiner* — Bin Shen
(74) *Attorney, Agent, or Firm* — Birch, Stewart, Kolasch & Birch, LLP

(57) ABSTRACT

Disclosed is a method for reducing measurement errors due to inhibition of catalase by azide in a method for quantification of a component to be measured, in which hydrogen peroxide derived from a component other than the component to be measured is decomposed by a catalase. The method for reducing measurement errors due to inhibition of catalase by azide employs a catalase which has a subunit having a molecular mass of 75 kDa or higher and is derived from a microorganism, when hydrogen peroxide derived from a component other than the component to be measured is decomposed by the catalase followed by quantification of hydrogen peroxide derived from the component to be measured to quantify the component to be measured.

5 Claims, No Drawings

METHOD OF REDUCING MEASUREMENT ERROR CAUSED BY CATALASE INHIBITION BY AZIDE

TECHNICAL FIELD

The present invention relates to a method for reducing measurement errors due to inhibition of catalase by an azide.

BACKGROUND ART

In the field of clinical tests, a method for measurement of the concentration of a compound to be measured in a test sample has been widely used, which method allows hydrogen peroxide to be generated from the compound to be measured, which hydrogen peroxide is then quantified in such a method, hydrogen peroxide generated from substances other than the component to be measured becomes a source of error. Therefore, a method wherein hydrogen peroxide generated from substances other than the component to be measured is decomposed to water and oxygen by the action of catalase; and a method using peroxidase wherein a phenol-based or aniline-based hydrogen donor compound is allowed to react with hydrogen peroxide to convert the hydrogen peroxide to a colorless quinone; are generally used to eliminate hydrogen peroxide. For example, they are used in a reagent for measurement of neutral fat, as a system for elimination of endogenous free glycerol; in a reagent for measurement of creatinine, as a system for elimination of creatine and sarcosine; and in a reagent for measurement of HDL-cholesterol or LDL-cholesterol, as a system for elimination of cholesterol in lipoproteins other than a component to be measured. Conventionally, in a measurement system using a catalase, the catalase derived from bovine is generally used.

Among these, an elimination system using catalase is frequently used, but it is sometimes disturbed by contamination of a compound which inhibits the catalase. Especially, contamination of azide inhibits catalase strongly even in cases where its amount is very small, and disturbs the elimination system, so that hydrogen peroxide derived from a component other than a component to be measured cannot be sufficiently eliminated, which leads to errors in measured values.

Since azides such as sodium azide are widely used in the field of clinical tests as antiseptics, it is highly probable that they are contaminated to measurement systems. Examples of known cases of contamination of azide to a measurement system include cases where azide is contained in a sample itself to be measured, cases where azide is dissolved into a measurement reagent through vaporization of the azide as hydrogen azide from an azide-containing reagent existing in the vicinity thereof, and cases where azide is contaminated to a measurement reagent from another azide-containing reagent through a reagent-collecting probe of an automatic analyzer.

[Patent Literature 1] JP 10-14596 A
[Patent Literature 2] JP 3164829 B
[Patent literature 3] JP 3058602 B

DISCLOSURE OF THE INVENTION

Problems to be Solved by the Invention

Accordingly, an object of the present invention is to provide a method for reducing measurement errors due to inhibition of catalase by azide, in a method for quantifying a component to be measured comprising the step of decomposing hydrogen peroxide derived from a component other than the component to be measured.

Means for Solving the Problems

The present inventors intensively studied to discover that catalases which have a subunit having a molecular mass of 75 kDa or higher and are derived from microorganisms are less sensitive to inhibition by azide than catalases derived from bovine which have been conventionally used, and inferred that, by using as a catalase used for a measurement system a catalase which has a subunit having a molecular mass of 75 kDa or higher and is derived from a microorganism, measurement errors due to inhibition of catalase by azide can be reduced, thereby completing the present invention.

That is, the present invention provides a method for reducing measurement 1.5 errors when hydrogen peroxide derived from a component other than a component to be measured is decomposed by a catalase followed by quantification of hydrogen peroxide derived from the component to be measured to quantify said component to be measured, said measurement errors being due to inhibition of the catalase by an azide, said method comprising using as said catalase a catalase which has a subunit having a molecular mass of 75 kDa or higher and is derived from a microorganism

Effects of the Invention

By the present invention, a method for reducing measurement errors due to inhibition of catalase by azide was first provided. By the present invention, components to be measured such as neutral fat, LDL cholesterol, HDL cholesterol and creatinine can be quantified more accurately than by the conventional methods.

BEST MODE FOR CARRYING OUT THE INVENTION

As described above, the present inventors surprisingly discovered that catalases which have a subunit having a molecular mass of 75 kDa or higher and are derived from microorganisms are less sensitive to inhibition by azide than catalases derived from bovine which have been conventionally used. The present invention is based on this discovery.

Single-function catalases which are here-containing catalases can be grouped into catalases having a small subunit (55 to 69 kDa) and catalases having a large subunit (not less than 75 kDa). The catalases used in the present invention are the above-described catalases having a large subunit (not less than 75 kDa).

Examples of microorganisms from which the above-described catalases used in the present invention are derived include those of fungi, bacteria and a part of archaebacteria, more particularly, *Podospora anserina, Neurospora crossa, Cladosporium fulvum, Emericella nidulans, Pleurotus ostreatus, Deinococcus radiodurans, Escherichia coli, Salmonella typhimurium, Pseudomonas putida, Psuedomonas putida, Bacillus subtilis, Bacillus subtillis, Bacillus firmus, Mycobacterium avium, Botryotinia fuckeliana, Claviceps purpurea, Aspergillus fumigatus, Ajellomyces capsulatus, Aspergillus nidulans, Aspergillus niger, Agrobacterium tumefaciens, Sinorhizobium meliloti, Mesorhizobium loti, Nosema locustae, Xanthomonas oryzae* and *Xanthotnonas campestris*. Although bacteria and the like are known to produce a plurality of types of catalases, those having a large subunit (not less than 75 kDa) are the catalases used in the method of the present invention. Even in cases where the above-described catalases having a small subunit are contained in the above-described catalases having a large subunit, the present invention can be carried out without any problem.

Examples of known catalases which are produced by the above-described microorganisms and have a large subunit (not less than 75 kDa) include *Podospora anserina* CatA, *Aspergillus fumigatus* CatA, *Emericella nidulans* CatA, *Ajellomyces capsulatus* CatA, *Escherichia Coli* KatE, *Escherichia coli* K12, *Pseudomonas putida* CatC, *Bacillus subtilis* catalase 2, *Bacillus subtilis* KatE, *Bacillus firmus* KatA, *Mycobacterium avium* KatE, *Aspergillus fumigalus* CatB, *Ajellomyces capsulatus* CatB, *Aspergillus nidulans* CatA, *Aspergillus niger* CatR, *Agrobacterium tumefaciens* CatC, *Sinorhizobium meliloti* CatC, *Nosema locustae*, *Xanthomonas oryzae* KatX and *Xanthomonas campestris* KatE. It is described in "Bacterial Catalase in the Microsporidian *Nosema locustae*: Implications for Microsporidian Metabolism and Genome Evolution" Naomi M. Fast et at, EUKARYOTIC CELL, October 2003, p. 1069-1075 that these catalases are genetically related to each other, and these catalases are known to have heme d. It is well-known that genetically-related enzymes have similar characteristics. Thus, the catalases used in the present invention is not limited to those listed above, and any catalase can be used in the method of the present invention as long as it is a genetically-related catalase which has heme d and a subunit having a molecular mass of 75 kDa or higher. Although the upper limit of the molecular mass of the large subunit is reported to be 84 kDa or 90 kDa, any genetically-related catalase can be used in the present invention. "Genetically related" means being regarded as related ones and grouped into the same group by a phylogenetic analysis by a conventional method based on amino acid sequences, so that, for example, the catalases grouped into the Group II by the method described in the above literature by Fast ei al, can be said to be genetically related to each other. As the catalase, either a single type or a mixture of a plurality of types of catalase(s) can be used. In cases where 2 or more types of catalases are used, these may be either catalases derived from the same type of microorganism or catalases derived from different types of microorganisms.

Various types of such microorganism-derived catalases are commercially available, and the commercially available products may preferably be employed. They can also be obtained by a conventional method which is well-known in the art, which method comprises steps of culturing of a microorganism and purification of a catalase from the culture.

Among azides which may be contaminated to a measurement system and inhibit catalase, those problematic in quantitative measurement of various components are mainly metal azides such as sodium azide mainly used as an antiseptic, and hydrogen azide derived therefrom and the like, but not limited thereto.

The method of the present invention is applicable to any method for quantification, which method comprises decomposition of hydrogen peroxide derived from a component other than a component to be measured by catalase, followed by quantification of hydrogen peroxide derived from the component to be measured to quantify the component to be measured. As such a quantification method itself, various methods are well-known in the art. Examples of the components to be measured include, but are not limited to, neutral fat (triglyceride), HDL (high density lipoprotein) cholesterol, LDL (low density lipoprotein) cholesterol and creatinine. The method of the present invention can be carried out by carrying out a conventional method, as it is, for quantification of each component to be measured except that a catalase which has a subunit having a molecular mass of 75 kDa or higher and is derived from a microorganism is used.

The method of the present invention comprises decomposition, by a catalase derived from a microorganism, of hydrogen peroxide derived from a component other than a component to be measured, followed by addition of azide. The catalase used in the method of the present invention is less sensitive to inhibition by azide, but the hydrogen peroxide-decomposing reaction of the catalase can be stopped by allowing a sufficient amount of azide to act thereon. By this method, it is possible to prevent decomposition, by the catalase, of hydrogen peroxide produced by the reaction for quantification.

The above-exemplified measurement method itself using a catalase, for measurement of various components to be measured is well-known and therefore it is not necessary to explain it in the present specification, but the method will be described briefly below.

Neutral fat (triglyceride) can be quantified by, for example, a process wherein glycerol kinase, glycerol-3-phosphate oxidase and catalase are allowed to act on glycerin contained in the body fluid, thereby eliminating hydrogen peroxide produced from the glycerin; and lipoprotein lipase, glycerol kinase, glycerol-3-phosphate oxidase, peroxidase and a chromogen are allowed to act on triglyceride in the body fluid to allow production of glycerin from the triglyceride, which glycerin produced is then allowed to produce glycerol-3-phosphate, which glycerol-3-phosphate is then allowed to produce hydrogen peroxide, which hydrogen peroxide is then colored, followed by measuring its color intensity (Patent Literature 1).

HDL cholesterol can be quantified by, for example, a process wherein cholesterol esterase and cholesterol oxidase are allowed to act on a test sample in a buffer solution maintaining a pH of 5 to 8 and in the presence of a divalent ion, and the resulting hydrogen peroxide is eliminated by catalase, thereby eliminating cholesterol in lipoproteins other than high density lipoproteins in the test sample, followed by addition of a surfactant which specifically acts on high density lipoproteins and have an HLB of 13 to 14 to the product in the first step, and quantification of hydrogen peroxide produced by the actions of the cholesterol esterase and the cholesterol oxidase to quantify cholesterol in the high density lipoproteins (Patent Literature 2).

LDL cholesterol can be quantified by, for example, a process wherein cholesterol esterase and cholesterol oxidase are allowed to act on a test sample in the presence of a buffer solution containing an amine and of a surfactant which acts on lipoproteins other than low density lipoproteins, and the resulting hydrogen peroxide is eliminated by catalase, thereby eliminating cholesterol in high density lipoproteins, very low density lipoproteins and chylomicron in the test sample, followed by quantification of the remaining cholesterol in the test sample (Patent Literature 3).

Creatinine can be quantified by, for example, a process wherein creatine amidinohydrolase, sarcosine oxidase and catalase are allowed to act on creatine contained in the body fluid and hydrogen peroxide generated from the creatine is eliminated, followed by allowing creatinine amidohydrolase, creatine amidinohydrolase, sarcosine oxidase, peroxidase and a chromogen to act on creatinine in the body fluid to allow generation of creatine from the creatinine, which creatine is then allowed to generate sarcosine, which is then allowed to generate hydrogen peroxide, which is then colored; and subsequently measuring its color intensity (Patent Literature 1).

The present invention will now be described more concretely by way of the Example below. However, the present invention is not restricted to the Example below.

EXAMPLES

Comparative Example 1, Example 1

As reagents for removal of endogenous free glycerol and measurement of neutral fat, a first reagent and a second reagent having the compositions below were prepared (Comparative Example 1).

| First reagent | PIPES buffer, pH 6.5 | 50 mmol/L |
|---|---|---|
| | Glycerol kinase | 1000 U/L |
| | Glycerol-3-phosphate oxidase | 5000 U/L |
| | Catalase (derived from bovine liver) | 300,000 U/L |
| | N-(2-hydroxysulfopropyl)-3,5-dimethoxyaniline | 0.3 mmol/L |
| | Adenosine 5'-triphosphate | 1.6 mmol/L |
| | Magnesium chloride | 7.5 mmol/L |
| | Polyethylene glycol mono-p-isooctyl phenyl ether | 0.3% |
| Second reagent | PIPES buffer, pH 6.5 | 50 mmol/L |
| | Lipoprotein lipase | 3000 U/L |
| | Peroxidase | 3000 U/L |
| | 4-Aminoantipyrine | 4.2 mmol/L |
| | Sodium azide | 0.1% |
| | Magnesium chloride | 7.5 mmol/L |
| | Polyethylene glycol mono-p-isooctyl phenyl ether | 0.3% |

On the other hand, the catalase in the first reagent of the above-described Comparative Example 1 was changed to one derived from *Aspergillus niger* (*Aspergillus niger* CatR, manufactured by Roche Diagnostics GmbH) to prepare a first reagent (Example 1).

To 4 of a sample (human serum) to which sodium azide was added to 0 to 0.1%, 300 µl of the first reagent prewarmed to 37° C. was mixed, and the resulting mixture was allowed to react at 37° C. for 5 minutes, followed by addition of 100 µl of the second reagent thereto; allowing the resulting mixture to react for 5 minutes; and measuring the absorbance thereof at 600 nm. From the measured absorbance, the amount of neutral fat was calculated to obtain the amount of neutral fat in the sample. The results of Comparative Example 1 and Example 1 are shown in Table 1.

TABLE 1

| Added amount of sodium azide (%) | Comparative Example 1 | Example 1 |
|---|---|---|
| 0.00 | 127.4 | 124.5 |
| 0.02 | 145.7 | 124.5 |
| 0.04 | 151.8 | 125.1 |
| 0.06 | 155.8 | 124.2 |
| 0.08 | 159.6 | 125.6 |
| 0.10 | 161.3 | 125.6 |

In Comparative Example 1, inhibition of elimination of the endogenous free glycerol increased as the added amount of sodium azide in the sample increased, which caused an increase in the measured value. On the other hand, in Example 1, an increase in the added amount of sodium azide hardly caused an increase in the measured value, which suggests that the elimination system was not substantially disturbed. By this, it can be seen that an accurate measurement can be carried out by the present invention since the elimination system by catalase is not substantially disturbed even by contamination of an azide.

The invention claimed is:

1. A method of reducing measurement errors when hydrogen peroxide derived from a component other than a component to be measured is decomposed by a catalase, comprising the steps of:
    decomposing said hydrogen peroxide in the presence of catalase and an azide; and
    quantifying hydrogen peroxide derived from the component to be measured to quantify said component to be measured, said measurement errors being due to inhibition of the catalase by an azide, and said catalase comprising a catalase which has a subunit having a molecular mass of 75 kDa or higher and is derived from a microorganism.

2. The method according to claim 1, wherein said catalase is a catalase having heme d.

3. The method according to claim 1, wherein said microorganism is an organism of at least one species selected from the group consisting of microorganisms belonging to the genera *Podospora*, *Neurospora*, *Cladosporium*, *Emericella*, *Pleurotus*, *Deinococcus*, *Escherichia*, *Salmonella*, *Pseudomonas*, *Bacillus*, *Mycobacterium*, *Botryotinia*, *Claviceps*, *Aspergillus*, *Ajellomyces*, *Agrobacterium*, *Sinorhizobium*, *Mesorhizobium*, *Nosema* and *Xanthomonas*.

4. The method according to claim 3, wherein said microorganism belongs to *Aspergillus*.

5. The method according to claim 1, wherein said component to be measured is neutral fat, HDL cholesterol, LDL cholesterol or creatinine.

* * * * *